United States Patent [19]
Rosen et al.

[11] Patent Number: 5,820,627
[45] Date of Patent: Oct. 13, 1998

[54] REAL-TIME OPTICAL FEEDBACK CONTROL OF LASER LITHOTRIPSY

[75] Inventors: David I. Rosen, Arlington; Charles L. Goldey, Boston, both of Mass.; Gary B. Hayes, Bedford, N.H.

[73] Assignee: Physical Sciences, Inc., Andover, Mich.

[21] Appl. No.: 623,070

[22] Filed: Mar. 28, 1996

[51] Int. Cl.$^6$ .................................................. A61B 17/36
[52] U.S. Cl. .................................. 606/15; 606/3; 606/12
[58] Field of Search .................................. 606/2, 4, 5, 6, 606/10, 11, 12, 14, 15, 16, 17

[56] References Cited

U.S. PATENT DOCUMENTS

| | | | |
|---|---|---|---|
| 4,718,417 | 1/1988 | Kittrell | 606/15 |
| 5,279,298 | 1/1994 | Flower | 606/4 |
| 5,279,611 | 1/1994 | McDonnell et al. | 606/5 |
| 5,354,323 | 10/1994 | Whitebook | 606/11 |
| 5,395,356 | 3/1995 | King et al. | 606/4 |
| 5,549,599 | 8/1996 | Sumiya | 606/10 |
| 5,569,242 | 10/1996 | Lax et al. | 606/42 |

OTHER PUBLICATIONS

Bhatta, et al., "Acoustic and Plasma Guided Lasertripsy (APGL) of Urinary Calculi," The Journal of Urology, (vol. 142, Aug., 1989) pp. 433–437.

Thomas, MD, et al., "The Pulsed Dye Laser Versus the Q–Switched Nd:YAG Laser–Induced Shock–Wave Lithotripsy," Lasers in Surgery and Medicine 8:363–370 (1988).

Scheu MSc, et al., "A New Concept for a Realtime Feedback System in Angioplasty with a Flashlamp Pumped Dye Laser," Lasers in Surgery and Medicine 11:133–140 (1991).

Bhatta, et al., "Acoustic and Plasma–Guided Laser Angioplasty," Lasers in Surgery and Medicine 9:117–123 (1989).

Boni, et al., "High–Power Laser Applications to Medicine," J. Quant. Spectrosc. Radiat. Transfer, (vol. 40, No. 3, pp. 449–467) 1988, Great Britain.

Teng, et al., "Optical Studies of Pulsed–Laser Fragmentation of Biliary Calculi," Applied Physics B 42, 73–78 (1987).

Englehardt, et al., "Spectroscopy During Laser Induced Shock Wave Lithotripsy," Optical Fibers in Medicine III SPIE (vol. 906, pp. 200–204) 1988.

Rosen, et. al., "Acoustical and Optical Feedback Guidance for Pulsed Laser Lithotripsy and Angioplasty," Laser Surgery: Advanced Characterization, Therapeutics, and Systems SPIE (vol. 1066, pp. 262–270), 1989.

Brinkman, et al., Laser Induced Shockwave Lithotripsy by Use of an 1 $\mu$s Alexandrite Laser, Laser Surgery: Advanced Characterization, Therapeutics, and Systems II SPIE (vol. 1200, pp. 67–74)1990.

Goldey, et al., "Development of a 'Smart' Ho:YAG Laser Lithoriptor: Results of Phase I Feasibility Study," ASLMS Meeting (20 pages), Apr., 1995.

Goldey, et al., "Development of a Smart Holmium:YAG Laser Lithoriptor," Abstract, ASLMS Proceedings (1 page), Apr., 1995.

Rosen, et al., "Real–time Optical Feedback Control of Laser Lithotripsy," SPIE (vol. 1879, 11 pages) 1993.

Rosen, D.I., "Smart Laser for Medical Laser Treatments," LEOS Conference, Sep. 1994 (2 pages).

Primary Examiner—Jennifer Bahr
Assistant Examiner—Sonya Harris-Ogugua
Attorney, Agent, or Firm—Testa, Hurwitz & Thibeault, LLP

[57] ABSTRACT

A method for selectively ablating targeted biological material uses real-time optical feedback control to measure incandescent photoemissions emitted from irradiated biological material and, based on the measured incandescent photoemissions, adjust laser pulse parameters to selectively ablate targeted biological material. Laser pulses are directed to a target area of the subject using a delivery system. During each laser pulse, incandescent photoemissions emitted from the biological material having a wavelength of less than that of the laser pulses are measured. Based on such measured incandescent photoemissions, at least one of the wavelenght, pulse duration and energy level of each laser pulse are adjusted in order to selectively ablate targeted soft or hard biological material.

20 Claims, 6 Drawing Sheets

REAL-TIME OPTICAL FEEDBACK CONTROL OF LASER LITHOTRIPSY

GOVERNMENT RIGHTS

The subject matter described herein was supported in part by National Institute of Health SBIR Grant No. 1R43 DK 48578-01.

FIELD OF THE INVENTION

This invention relates to a method for selectively detecting and ablating biological material in a subject. More particularly, this invention relates to a real-time optical feedback control method for selectively detecting and ablating targeted (soft or hard) biological material within a subject based on measured incandescent photoemissions emitted from such biological materials.

BACKGROUND

Over the past several years, the laser surgeons and researchers have begun to appreciate the benefits of pulsed lasers, instead of continues wave lasers, for controlled and precise tissue removal. Pulsed lasers are being more frequently used by laser surgeons to perform ablation procedures that, in the past, were performed using continuous wave $CO_2$, argon, or Nd:YAG lasers.

The pulsed holmium solid state laser has recently become more popular for applications in orthopedic, vascular, urologic, and otolaryngolic surgery. The holmium laser is a relatively inexpensive solid state laser capable of emitting high energy, high peak power laser pulses. The pulses have a characteristic wavelength (i.e., 2.1 microns) that (i) enables them to be transmitted down a flexible glass fiber and (ii) is strongly absorbed by water with an absorption depth which permits efficient absorption by most biological materials, yet penetrates deep enough to be hemostatic. The holmium laser is a "non-discriminating" tissue ablator in that it ablates soft tissue and bone, calculi, and other hard tissues.

The characteristic of being a "non-discriminating" tissue ablator can also be a shortcoming of the holmium laser. Two reported investigations involving the holmium laser for endoscopic lithotripsy found that while the holmium laser can effectively be used to ablate urinary calculi, extreme care must be exercised to avoid ablating or damaging surrounding urinary tract tissue. This was shown to be particularly true when operating the holmium laser at energies over 0.5 joules per pulse. Unfortunately, it has been found that an energy of one joule per pulse is needed to achieve desired stone fragmentation rates. These investigations demonstrate the obvious need for significantly improving the margin of safety associated with performing lithotripsy using a pulsed holmium laser.

In the past decade, various groups have developed control systems based on various soft/hard tissue detection methods for laser lithotriptors. Most of these detection methods have been developed for a pulsed dye laser lithotriptor having a pulse wavelength of 504 or 590 nanometers. One group, however, has applied its detection method to an alexandrite laser lithotriptor having a pulse wavelength of 780 nanometers. This latter group uses the alexandrite laser to perform laser-induced shockwave lithotripsy. Another known control system described in U.S. Pat. No. 4,939,336 uses a soft/hard tissue detection method for a laser operating at an excitation wavelength less than 1000 nanometers. The detection method determines tissue type based on differences between the laser-induced "fluorescence" emitted by soft and hard tissue in the 650 to 1000 nanometer range.

SUMMARY OF THE INVENTION

The present invention features a method (and apparatus) for selectively ablating targeted biological material using real-time optical feedback control to measure incandescent photoemissions emitted from irradiated biological material and, based on the measured incandescent photoemissions, adjust laser pulse parameters to selectively ablate targeted biological material. The term "incandescent photoemissions" or "incandescence" is defined herein to mean the thermally-induced radiation emitted from the surface of the biological material or from a plasma-induced on the surface. These incandescent photoemissions are thermally induced during an initial portion of the laser pulse. The differences between the laser-induced incandescent photoemissions emitted by hard and soft biological material are measured by a feedback control system. Laser pulse parameters are adjusted based on such measured incandescent photoemissions in order to selectively ablate targeted soft or hard biological material.

In one embodiment, the invention features a method for selectively ablating targeted hard or soft biological material within a subject. Infrared laser pulses are generated by a pulsed infrared laser. The laser pulses are directed to a target area of the subject using a fiber optic delivery system. During select infrared laser pulses, incandescent photoemissions that are emitted from the target area at a wavelength less than the wavelength of the infrared laser pulses are measured by the feedback control system. Based on the measured incandescent photoemissions, the control system determines whether the target area corresponds to targeted biological material or non-targeted biological material. At least one of the wavelength, pulse duration and energy level of the infrared laser pulses are adjusted to selectively ablate targeted biological material and preserve non-targeted biological material.

In a more detailed embodiment, a pulsed solid-state laser generates laser pulses having a wavelength of between 1000 and 3000 nanometers, a pulse duration of between 1 and 500 microseconds and an energy level of between 20 and 2500 millijoules. A fiber optic delivery system directs the laser pulses to a target area of the subject. The control system measures, during each laser pulse, incandescent photoemissions emitted from the target area at a wavelength which is less than the wavelength of the laser pulse. The control system determines, based on the measured incandescent photoemissions, whether the target area corresponds to targeted biological material or non-targeted biological material. The control system then adjusts at least one of the wavelength, pulse duration and energy level of each laser pulse to selectively ablate targeted biological material and preserve non-targeted biological material. That is, the control system may interrupt the laser pulses when the measured incandescent photoemissions are less than (or greater than) a threshold value, to thereby prevent ablation of non-targeted biological material.

Targeted biological material may be hard tissue such as urinary calculi, biliary calculi, salivary calculi, calciferous plaque, bones or teeth. Alternatively, targeted biological material may be soft tissue such as dermal tissue, urinary tract tissue, biliary tract tissue, vascular tissue, dental tissue, cartilage or ligament.

BRIEF DESCRIPTION OF THE DRAWINGS

These and other features of the invention are more fully described below in the detailed description and accompanying drawings of which the figures illustrate the method (and apparatus) for selectively detecting and ablating biological material in a subject using real-time optical feedback control.

DETAILED DESCRIPTION

The present invention features a method (and apparatus) for selectively ablating targeted hard or soft biological material based on incandescent photoemissions measured using a real-time optical feedback control system. These incandescent photoemissions are thermally induced during an initial portion of each laser pulse. The differences between the incandescent photoemissions emitted by hard and soft biological material are measured by a feedback control system, and laser pulse parameters are adjusted to selectively ablate targeted soft or hard biological material. With this approach, in contrast to fluorescence detection methods, there is less restriction on the laser pulse wavelength. The only requirement is that the wavelength be absorbed strongly enough by the targeted material to generate a rapid and radiometrically measurable temperature rise.

Figure 1A:
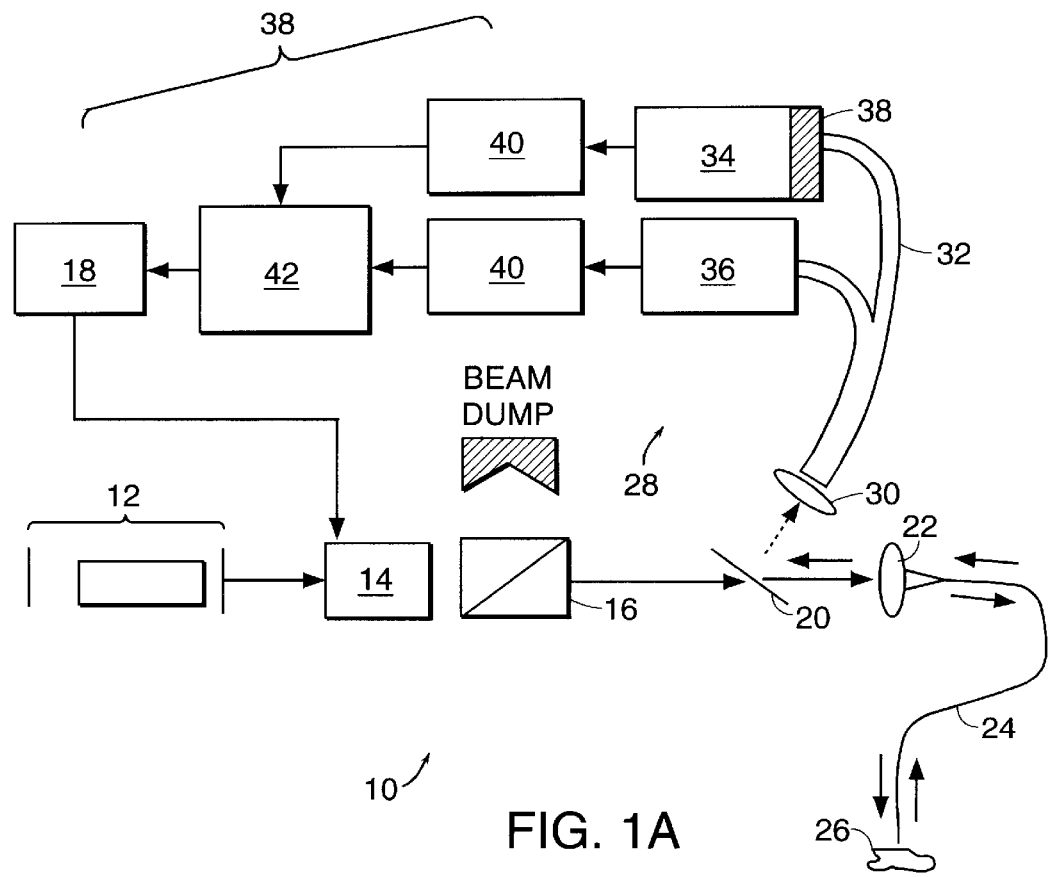
FIG. 1A is a block diagram of an apparatus including a feedback control system for a laser incorporating the principles of the invention.

FIG. 1 is a block diagram of an apparatus including a feedback control system for a pulsed laser. The apparatus 10 includes a solid-state pulsed infrared laser 12 that provides a pulsed output beam having a wavelength of between 1000 and 3000 nanometers, pulse duration of between 1 and 500 microseconds and energy level of between 20 and 2500 millijoules. In one embodiment, the laser 12 is a holmium laser (e.g., a Coherent Medical Versa Pulse Model 3000) operating at 2.1 microns.

The output beam is directed to a fast electro-optic beam shutter 14 (e.g., a Pockels cell) followed by a calcite beam polarizer 16. The beam shutter is anti-reflection coated for minimum reflectance losses at 2.1 microns. A high-voltage driver 18 controls the shutter 14. Under normal operation, the phase of the shutter 14 and orientation of the polarizer 16 are arranged to allow maximum transmission of the linearly polarized pulsed output beam. Thus, at the start of each pulse, the beam shutter 14 is configured for maximum transmission.

After passing through the shutter 14 and polarizer 16, the pulsed output beam passes through a dichroic beam splitter 20 and is focused by a lens 22 into a flexible optical fiber 24. The fiber directs the pulsed beam to a target area 26 of a patient. Laser-induced incandescent photoemissions are emitted from the target area 26 during each pulse. These thermal emissions are transmitted retrograde from the target area 26 back though the fiber 24 and reflected from the beam splitter 20 to an optical feedback control system 28.

The optical feedback control system 28 includes a lens 30 for focusing the induced incandescent photoemissions into a bifurcated quartz fiber bundle 32. The bundle 32 is coupled to two fast silicon photodiodes 34, 36 equipped with a series of spectral bandpass filters 38. The filters were chosen to transmit incandescent photoemissions in the wavelength interval of interest (i.e., incandescent photoemissions emitted at a wavelength which is less than the wavelength of the laser) while strongly rejecting scattered light at the laser wavelength.

Figure 2:
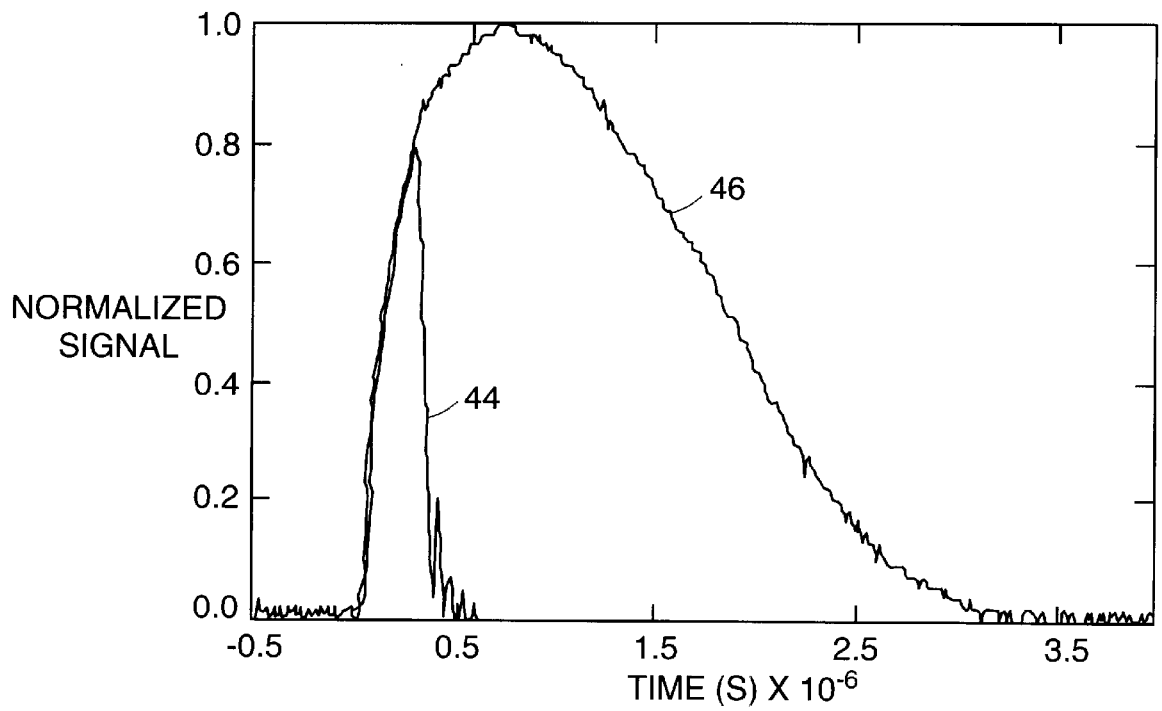
FIG. 2 is a graphical representation of the output spectra for laser pulses for the apparatus of FIG. 1.

The signal outputs from the photodiodes 34, 36 are detected by control electronics 38, which includes level comparators 40, pulse timing/logic circuitry 42, and the high-voltage driver 18. This circuitry enables a user to preset a threshold photoemission signal level, at a selected time early in each laser pulse, to indicate contact with targeted tissue (e.g., a calculus). If this threshold amplitude level is not reached, the driver 18 causes the shutter 14 to close, interrupting the laser pulse and preventing any further discharge of laser energy from that pulse. If, however, the threshold amplitude level is reached, the driver 18 enables the shutter 14 to remain open, providing complete discharge of laser energy from that pulse. The profiles of an interrupted laser pulse 44 and a full pulse 46 are shown in FIG. 2. Thus, full laser pulse energy is transmitted through the fiber 24 when the laser-induced incandescent photoemission intensity exceeds a chosen discrimination level; otherwise the laser pulse is switched off rapidly ensuring that no further laser energy is delivered to the subject.

In operation, a laser surgeon adjusts the pulse parameters of the laser and using the fiber optic delivery system irradiates a target area of a patient. The control system measures, during each laser pulse, incandescent photoemissions emitted from the target area at a wavelength which is less than the wavelength of the laser pulse. The control system determines, based on the measured incandescent photoemissions, whether the target area corresponds to targeted biological material or non-targeted biological material. The control system then adjusts at least one of the wavelength, pulse duration and energy level of each laser pulse to selectively ablate targeted biological material and preserve non-targeted biological material.

Experimental Results

Figure 1B:
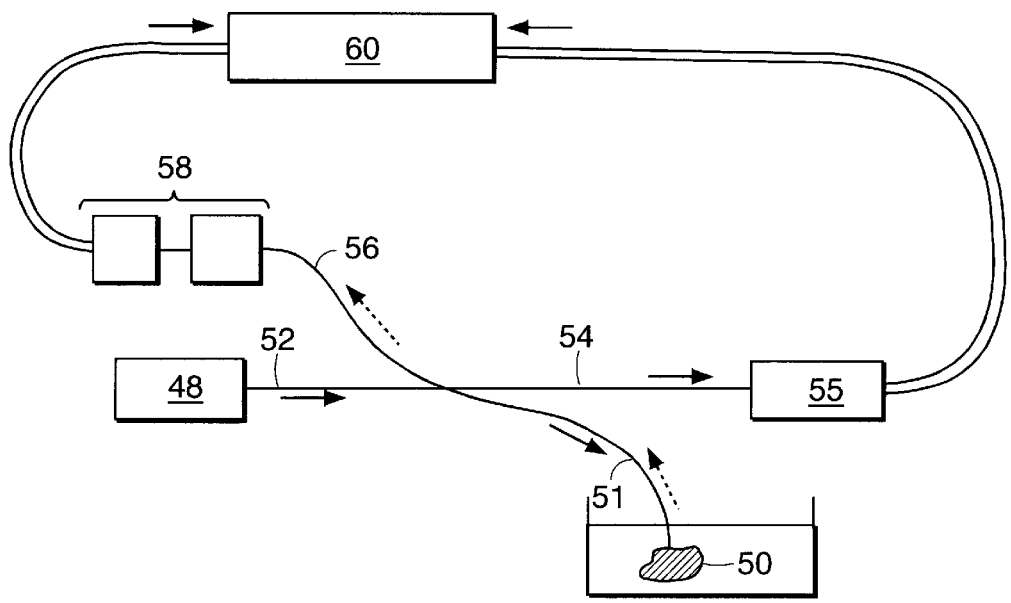
FIG. 1B is a block diagram of a laser apparatus used to collect incandescent photoemission data for various hard and soft biological materials.

FIG. 1B is a block diagram of a laser apparatus used to collect incandescent photoemission data for various hard and soft biological materials. A holmium laser 48 delivers pulses to a tissue specimen 50 via one leg 51 of a bifurcated (2×2), 400-μm core diameter, low OH Si/Si fiber 52. The distal end of the other fiber leg 54 is directed to a room temperature detector 55 that monitors the laser output pulse. The proximal end of the other fiber leg 56 is directed to a detection system 58 that monitors the laser-induced incandescent photoemissions emitted from the tissue specimen 50. Photoemission data is digitally recorded and stored on a personal computer 60 for subsequent analysis.

Preliminary in vitro incandescent photoemission data has been collected which supports the viability of the technique. Data were first obtained using the diode array spectrograph detection system 60 with the array triggered at the start of each laser pulse and set to a gate width of 0.1 ms. Spectral emissions from approximately 350 to 850 nanometers were measured. A holmium laser energy of approximately 0.8 J was delivered to each specimen via a 400-$\mu$m core fiber and the resulting photoemission recorded. The specimens were irradiated in a saline bath and with direct fiber contact.

Figure 3A:
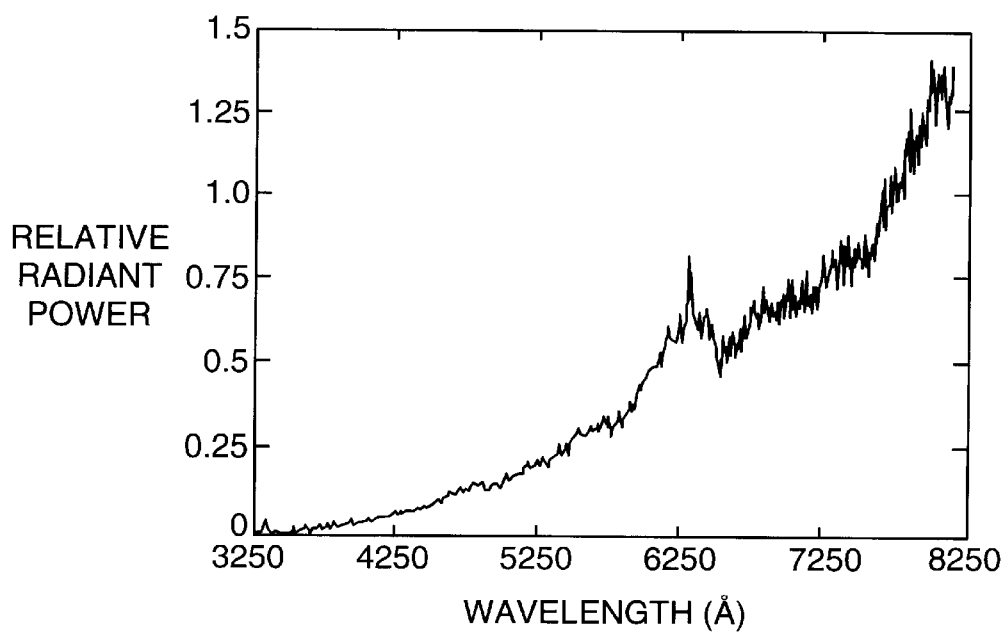
FIGS. 3A–3C are graphical representations of laser-induced photoemission spectra for hard biological materials (i.e., a calcium oxalate stone and a urinary stone, respectively) and a soft biological material (i.e., bovine bladder tissue).
Figure 3B:
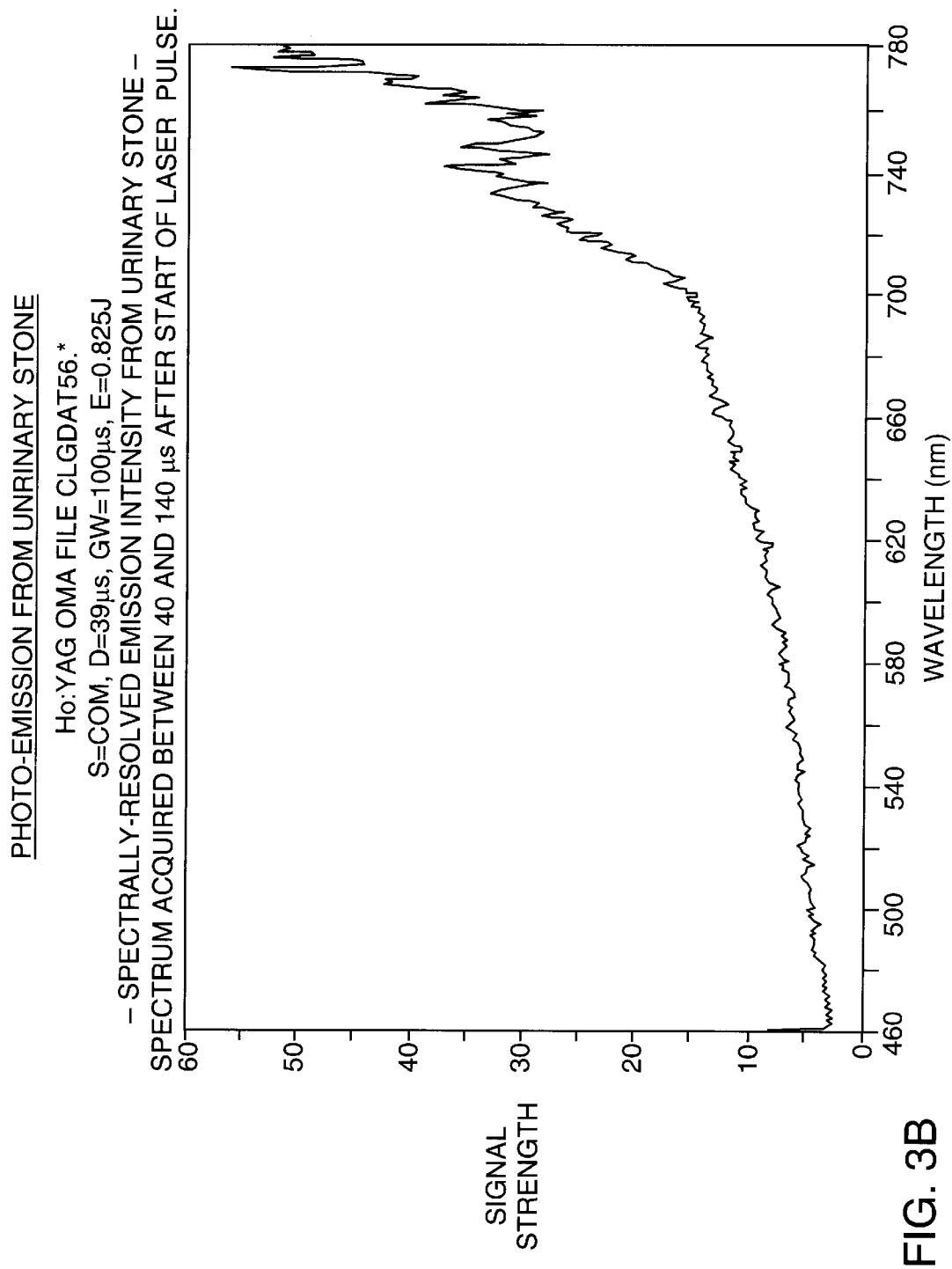
Figure 3C:
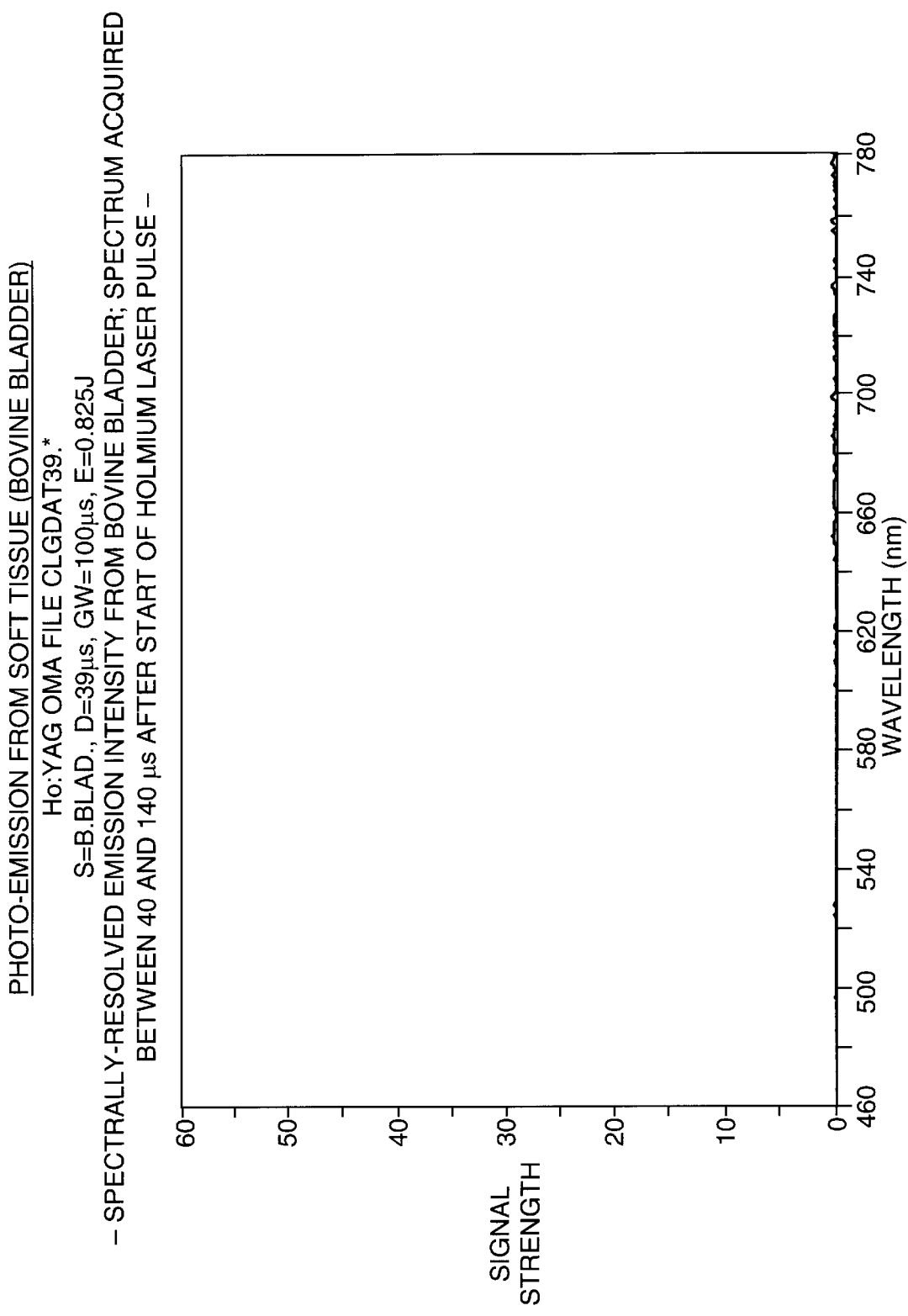

FIG. 3A–3C represent response-corrected photoemission spectrum for the calculi tested. As shown, strong photoemissions were observed from all calculi tested, including calcium oxalate, struvite/apatite, and cystine stones. These photoemissions appeared dominantly as a continuum throughout the visible and near-infrared with the radiant power increasing monotonically from 350 to 830 nanometers. Under similar test conditions, no detectable laser-induced photoemissions were observed from the soft tissue specimens tested or from normal saline.

These results further support the view that the observed photoemission is thermal in origin. It is believed that the observed laser-induced calculi photoemissions result from rapid heating of the calculi to incandescent temperatures, possibly followed by plasma formation. For rapid intrapulse feedback control, the calculus photoemission must be detected sufficiently early in the laser pulse, i.e., early enough that a major portion of the pulse can be interrupted if the laser pulse is not being discharged on targeted calculi. To this end, the diode array spectrograph is replaced with a single silicon photodetector to monitor the "onset time" of the calculi photoemissions. For these experiments, the photodetector was operated without a bandpass filter and was therefore able to detect all light emitted between 350 and 1000 nanometers. The detector was also allowed to be driven to saturation.

Figure 4:
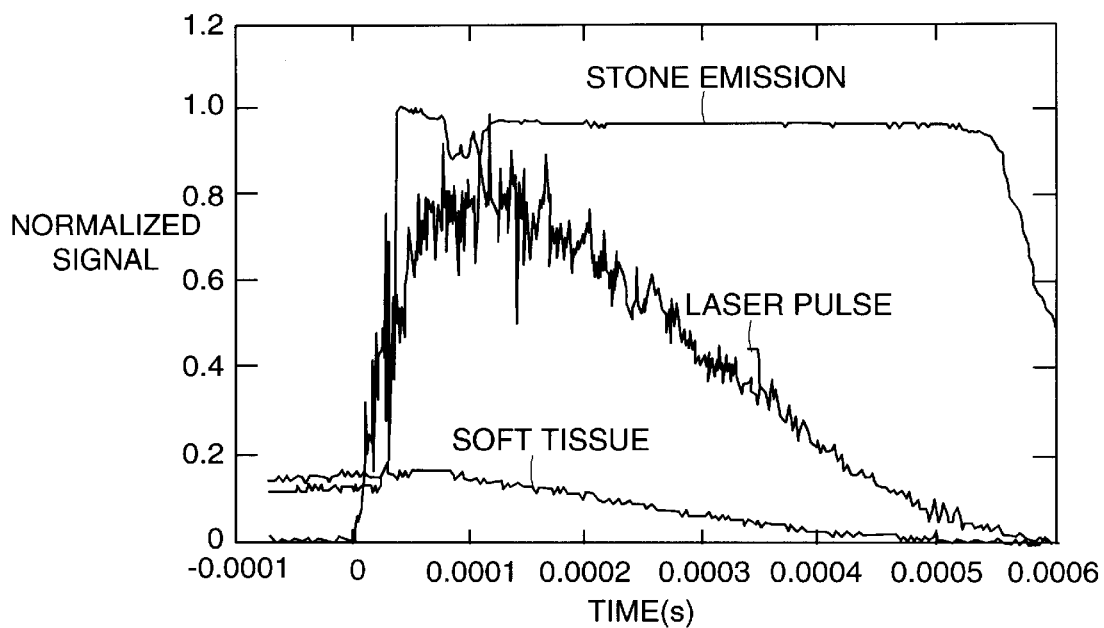
FIG. 4 is a graphical representation of laser-induced photoemission spectra for targeted hard biological material, non-targeted soft biological material and a laser pulse history profile.
Figure 5:
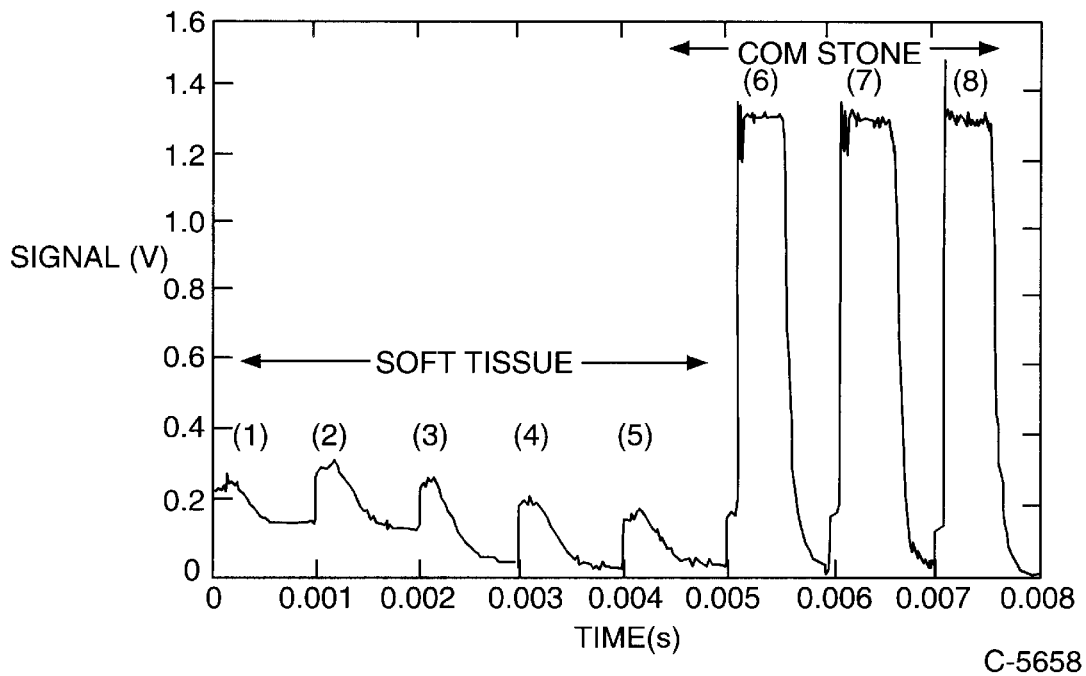
FIG. 5 is a graphical representation of laser-induced photoemission spectra for non-targeted soft and targeted hard biological materials for a sequence of successive laser pulses.

FIG. 4 shows saturated photoemission spectra for a calcium oxalate stone, soft tissue and the laser pulse. As shown, the onset of strong emission from the stone occurs within 30 microseconds of the start of the pulse. FIG. 5 shows photoemission spectra for a sequence of eight successive laser pulses, with the first five pulses being discharged on soft tissue and the last three on a calculus. As can be seen, the photoemission levels for the soft tissue are quite different from the calculus.

Figure 6:
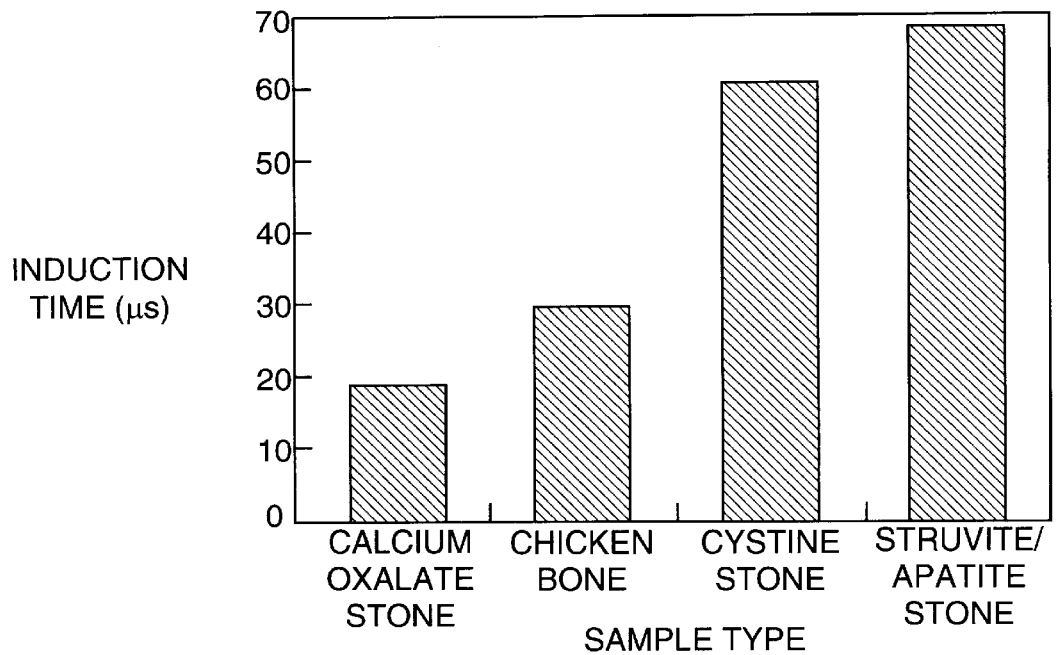
FIG. 6 is a graphical representation of the mean induction time for the generation of strong laser-induced photoemissions for various hard biological materials.
Figure 7:
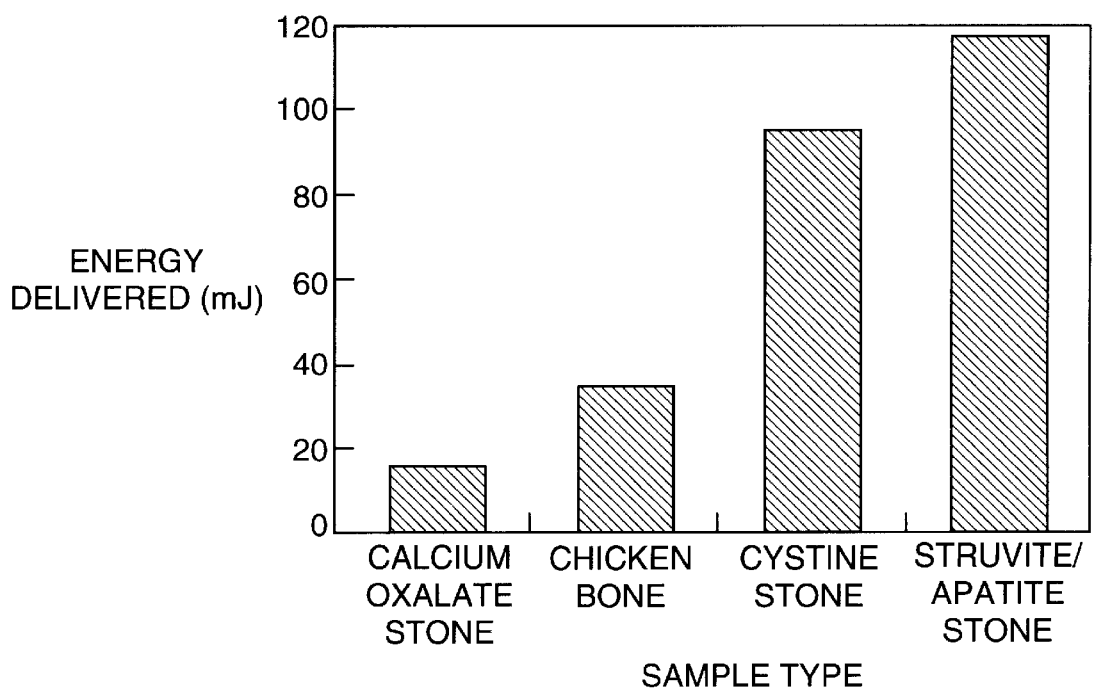
FIG. 7 is a graphical representation of the mean energy deposited prior to the generation of strong laser-induced photoemissions for the biological materials of FIG. 6.

FIGS. 6 and 7 are bar graphs showing photoemission data collected for a variety of calculi. In FIG. 6, the mean induction time to "strong emission onset" measured for the various calculi and a chicken thigh bone is plotted. The term "strong emission onset" is defined herein as the point in time at which the emission signal first clearly rises above the observed background levels. As shown, the onset times vary from a minimum of about 20 microseconds for calcium oxalate stones to a maximum of about 70 microseconds for struvite stones.

The data shown in FIG. 6 were further used to estimate the amount of laser energy delivered up to the point of emission signal "onset". This was done by integrating the holmium laser pulse shape up to the various onset times and comparing that integral to the total pulse integral. The results are shown in the bar graphs in FIG. 7. It is noted that while the energies required to induce strong calculus emission vary with calculus type, the induction energies are all less than 0.1 J. These data indicate that after delivering less than 0.1 J from the delivery fiber, it should be possible to determine if the holmium pulse is being discharged on a calculus and to terminate the laser pulse if it is not, thereby reducing the exposure risk to urinary tract tissue substantially.

While the invention has been particularly shown and described with reference to specific preferred embodiments, it should be understood by those skilled in the art that various changes in form and detail may be made therein without departing from the spirit and scope of the invention as defined by the appended claims. For example, while detailed embodiments of the invention include a holmium laser, other lasers such as a $CO_2$ laser (operating at a wavelength of 9–11 microns) may be used without departing from the scope of the claimed invention.

What is claimed is:

1. A method for selectively ablating targeted biological material within a subject comprising:

generating infrared laser pulses using a pulsed infrared laser;

directing the laser pulses to a target area of the subject using a delivery system coupled to the laser;

measuring, during select infrared laser pulses, thermally-induced radiation emitted from the target material at a wavelength less than the wavelength of the infrared laser pulses;

determining, based on the measured thermally-induced radiation, whether the target area corresponds to targeted biological material or non-targeted biological material; and adjusting at least one of the wavelength, pulse duration and energy level of the infrared laser pulses to selectively ablate targeted biological material and preserve non-targeted biological material.

2. The method of claim 1 wherein the laser is a pulsed holmium laser.

3. The method of claim 1 wherein the targeted biological material is hard tissue and non-targeted biological material is soft tissue or bodily fluids.

4. The method of claim 1 wherein the targeted biological material is soft tissue and non-targeted biological material is hard tissue.

5. The method of claim 1 further comprising generating laser pulses having a wavelength of between 1000 and 3000 nanometers or 9000 and 11000 nanometers.

6. The method of claim 1 further comprising generating laser pulses having a pulse duration of between 1 and 500 microseconds.

7. The method of claim 1 further comprising generating laser pulses having an energy level of between 20 and 2500 millijoules.

8. The method of claim 1 further comprising interrupting the laser pulses when the measured thermally-induced radiation is less than a threshold value, to thereby prevent ablation of non-targeted biological material.

9. The method of claim 1 further comprising interrupting the laser pulses when the measured thermally-induced radiation is greater than a threshold value, to thereby prevent ablation of non-targeted biological material.

10. The method of claim 1 wherein the targeted biological material comprises urinary calculi, biliary calculi, salivary calculi, calciferous plaque, bones or teeth.

11. The method of claim 1 wherein the non-targeted biological material comprises dermal tissue, urinary tract tissue, biliary tract tissue, vascular tissue, dental tissue, cartilage or ligament.

12. A method for selectively ablating targeted biological material within a subject comprising:

generating laser pulses using a pulsed laser having a wavelength of between 1000 and 3000 nanometers or 9000 and 11000 nanometers, a pulse duration of between 1 and 500 microseconds and an energy level of between 20 and 2500 millijoules;

directing the laser pulses to a target area of the subject using a delivery system coupled to the laser;

measuring, during each laser pulse, thermally-induced radiation emitted from the target material at a wavelength which is less than the wavelength of the laser pulse;

determining, based on the measured thermally-induced radiation, whether the target area corresponds to targeted biological material is non-targeted biological material;

adjusting at least one of the wavelength, pulse duration and energy level of each laser pulse to selectively ablate targeted biological material and preserve non-targeted biological material.

13. The method of claim 12 wherein the thermally-induced radiation occurs during an initial portion of the laser pulse.

14. The method of claim 12 wherein the laser is a pulsed holmium laser.

15. The method of claim 12 further comprising interrupting the laser pulses when the measured thermally-induced radiation is less than a threshold value, to thereby prevent ablation of non-targeted biological material.

16. The method of claim 12 further comprising interrupting the laser pulses when the measured thermally-induced radiation is greater than a threshold value, to thereby prevent ablation of non-targeted biological material.

17. The method of claim 12 wherein the targeted biological material is hard tissue and non-targeted biological material is soft tissue or bodily fluids.

18. The method of claim 12 wherein the targeted biological material is soft tissue and non-targeted biological material is hard tissue.

19. The method of claim 12 wherein the directing step further comprises delivering the laser pulses using an optical fiber delivery system connected to the pulsed laser.

20. A method for selectively ablating targeted mineral-rich biological material within a subject comprising:

generating laser pulses using a pulsed laser having a wavelength of between 1000 and 3000 nanometers or 9000 and 11000 nanometers, a pulse duration of between 1 and 500 microseconds and an energy level of between 20 and 2500 millijoules;

directing the laser pulses to a target area of the subject using a fiber optic delivery system coupled to the laser;

measuring, during an initial portion of each laser pulse, thermally-induced radiation emitted from the target material at a wavelength which is less than the wavelength of the laser pulse;

determining, based on the measured thermally-induced radiation, whether the target area corresponds to targeted mineral-rich biological material or non-targeted biological material;

adjusting at least one of the wavelength, pulse duration and energy level of each laser pulse to selectively ablate targeted mineral-rich biological material and preserve non-targeted biological material.

* * * * *

UNITED STATES PATENT AND TRADEMARK OFFICE
CERTIFICATE OF CORRECTION

PATENT NO. : 5,820,627
DATED : October 13, 1998
INVENTOR(S) : Rosen et al.

It is certified that error appears in the above-identified patent and that said Letters Patent is hereby corrected as shown below:

On the title page, item [73], should read:

Assignee: Physical Sciences, Inc., Andover, Mass.

Signed and Sealed this

Eighteenth Day of May, 1999

*Attest:*

Q. TODD DICKINSON

*Attesting Officer*     *Acting Commissioner of Patents and Trademarks*